United States Patent
Williams

(10) Patent No.: US 9,554,798 B2
(45) Date of Patent: Jan. 31, 2017

(54) SYSTEM AND METHOD FOR FORMING A T-SHAPED SURGICAL CLIP

(71) Applicant: Covidien LP, Mansfield, MA (US)

(72) Inventor: Justin Williams, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 631 days.

(21) Appl. No.: 13/865,484

(22) Filed: Apr. 18, 2013

(65) Prior Publication Data

US 2013/0338683 A1 Dec. 19, 2013

Related U.S. Application Data

(60) Provisional application No. 61/659,105, filed on Jun. 13, 2012.

(51) Int. Cl.
| | | |
|---|---|---|
| *A61B 17/08* | (2006.01) | |
| *A61B 17/10* | (2006.01) | |
| *A61B 17/122* | (2006.01) | |
| *A61B 17/128* | (2006.01) | |

(52) U.S. Cl.
CPC .............. *A61B 17/083* (2013.01); *A61B 17/10* (2013.01); *A61B 17/122* (2013.01); *A61B 17/1285* (2013.01)

(58) Field of Classification Search
CPC .................. A61B 2017/1107; A61B 17/1227; A61B 17/1285; B42F 1/02; B42F 1/04; B42F 1/06; B42F 1/08; B42F 1/10; B42F 1/12; Y10S 27/901; Y10S 27/902
See application file for complete search history.

(56) References Cited

U.S. PATENT DOCUMENTS

| | | | | |
|---|---|---|---|---|
| 4,489,875 A | * | 12/1984 | Crawford | ........... A61B 17/0644 227/19 |
| 4,874,122 A | | 10/1989 | Froehlich et al. | |
| 4,899,745 A | * | 2/1990 | Laboureau | ......... A61B 17/0684 411/457 |

(Continued)

FOREIGN PATENT DOCUMENTS

| | | |
|---|---|---|
| EP | 0 609 612 A2 | 8/1994 |
| EP | 0609612 | 8/1994 |
| EP | 1 554 984 A2 | 7/2005 |

OTHER PUBLICATIONS

European Office Action for EP 13 171 589.8 dated Jun. 11, 2015.
European Search Report dated Oct. 24, 2013 for EP 13 17 1589.

*Primary Examiner* — Ryan J Severson
*Assistant Examiner* — Christian Knauss

(57) ABSTRACT

A surgical clip forming apparatus includes an unformed surgical clip having a head section including an upper portion and a lower portion separated from each other to define a first space therebetween in a first configuration, a left leg section including a proximal end and a distal end and a right leg section including a proximal end and a distal end. The surgical clip forming apparatus includes an anvil configured to engage the head section of the surgical clip and a pair of forming pins positioned adjacent the proximal ends of the left and right legs for securing the head section of the unformed surgical clip against the anvil. When a force is applied to the anvil, the upper portion compresses toward the lower portion. The unformed surgical clip transforms into a "T-shaped" clip or a formed clip in a second configuration, after the force has been applied to the anvil.

24 Claims, 5 Drawing Sheets

(56) References Cited

U.S. PATENT DOCUMENTS

| | | | |
|---|---|---|---|
| 5,171,250 | A | 12/1992 | Yoon |
| 5,201,900 | A | 4/1993 | Nardella |
| 5,236,440 | A | 8/1993 | Hlavacek |
| 5,354,306 | A | 10/1994 | Garvey, III et al. |
| 5,425,740 | A | 6/1995 | Hutchinson, Jr. |
| 5,487,746 | A | 1/1996 | Yu et al. |
| 5,620,452 | A | 4/1997 | Yoon |
| 5,626,587 | A * | 5/1997 | Bishop ............... A61B 17/0682 227/175.1 |
| 5,846,255 | A | 12/1998 | Casey |
| 6,293,756 | B1 * | 9/2001 | Andersson .......... F04B 11/0058 417/3 |
| 6,293,956 | B1 | 9/2001 | Crainich et al. |
| 6,610,073 | B1 | 8/2003 | Levinson |
| 7,896,896 | B2 | 3/2011 | Viola |
| 8,287,559 | B2 | 10/2012 | Barker et al. |
| 8,372,095 | B2 | 2/2013 | Viola |
| 2007/0173866 | A1 | 7/2007 | Sorrentino et al. |
| 2009/0076533 | A1 | 3/2009 | Kayan et al. |

\* cited by examiner

SYSTEM AND METHOD FOR FORMING A T-SHAPED SURGICAL CLIP

CROSS-REFERENCE TO RELATED APPLICATIONS

This application claims the benefit of and priority to U.S. Provisional Patent Application No. 61/659,105, filed Jun. 13, 2012, the entire disclosure of which is incorporated by reference herein.

BACKGROUND

Technical Field

The present disclosure relates to minimally invasive surgery, and more particularly, to a system and method for forming a T-shaped surgical clip for occluding a blood vessel.

Background of Related Art

Minimally invasive surgery has grown in popularity in the past decade. Minimally invasive surgery (MIS) allows a surgeon to treat a patient while making only tiny incisions in the patient's body, through which surgical devices called cannulae are inserted. A cannula is essentially a thin, hollow tube through which other surgical tools may be inserted into and withdrawn from the patient's body. Because only a small incision is made in the patient's skin for insertion of a cannula, the patient heals faster and experiences less pain than in the aftermath of conventional surgery, in which larger incisions and tools are used.

In several minimally invasive procedures, blood vessels in a patient are permanently occluded. Two common procedures involving blood vessel occlusion are saphenous vein harvest, in which a vein and its branches are occluded so that a portion of that vein can be removed from one location in the body and used in another, and subfascial endoscopic perforator surgery, in which perforator veins are permanently occluded. In recent years, malleable metal clips or surgical hemostatic clips have been used for permanent occlusion. These clips typically have an opening at one end that is at least as wide as the blood vessel to be occluded. A surgical instrument is inserted through the cannula which places these clips, often serially, in desired locations on blood vessels, then squeezes them shut to achieve permanent occlusion. Such surgical instruments have in the past been bulky enough to require a cannula having an internal diameter of 10 mm or even 12 mm in order to insert them through the cannula to reach the operative site.

Certain factors are important to the performance of a surgical hemostatic clip to achieve proper tissue exudation and occlusion. The clip should not slip or become dislodged from a vessel after it has been applied. If the clip is not securely positioned, blood or other bodily fluid may begin flowing into the surgical site through the unclamped vessel. As a result, a surgeon locates and reclamps the vessel. Depending upon the type and location of the surgery, reclamping the vessel may be difficult, and reduce an overall productivity of the procedure. A clip should fully and completely close about a vein, artery, vessel or other conduit and completely stop the flow of blood or fluid therethrough. A clip that does not completely occlude the blood or fluid flow may have to be removed, thus requiring application of a second clip.

Some surgical hemostatic clips are U-shaped or V-shaped. These clips have a pair of legs joined at one end by an apex or crown and spaced apart at the opposed ends to define a gap between the legs. The desired vessel is introduced in the gap and the legs are compressed. The clip thus occludes the vessel using the legs. The legs have surfaces that contact tissue. These "tissue gripping surfaces" of the hemostatic clip may be made in a manner to improve the occluding functions of the hemostatic clip. The surfaces may also restrict dislocation of the hemostatic clip after it has been applied to the target blood vessel.

However, the legs often have a relatively small tissue gripping surface. Care must be taken when designing such tissue gripping surfaces to ensure that the most productive use of the relatively small tissue gripping surface is made to accomplish the occlusion. A significant aspect of the tissue gripping surfaces is this retention of the hemostatic clip on the tissue. Accordingly, there is a need in the art for an improved surgical hemostatic clip to provide an optimum vessel occlusion and optimal clip retention on tissue during a surgical procedure.

SUMMARY

In accordance with an embodiment of the present disclosure, there is provided a surgical clip forming apparatus including an unformed surgical clip having a head section including an upper portion and a lower portion, the upper and lower portions separated from each other to define a first space therebetween in a first configuration, a left leg section including a proximal end and a distal end, and a right leg section including a proximal end and a distal end. The surgical clip forming apparatus further includes an anvil configured to engage the head section of the surgical clip and a pair of forming pins positioned adjacent the proximal ends of the left and right legs for securing the head section of the unformed surgical clip against the anvil. When a force is applied to the anvil, the upper portion of the head section compresses toward the lower portion of the head section in order to establish a formed clip.

In an embodiment, the force applied to the anvil is a linear compression force.

In another embodiment, the lower portion of the head section includes a gap region between the pair of forming pins in the first configuration.

In yet another embodiment, the unformed surgical clip transforms into a "T-shaped" clip, which is the formed clip in a second configuration, after the force has been applied to the anvil, such that the upper and lower portions are separated from each other to define a second space therebetween, the second space being less than the first space.

In another embodiment, the gap region disappears after the force has been applied to the anvil in the second configuration.

In yet another embodiment, the left and right legs extend in a substantially parallel configuration relative to each other after the force has been applied to the anvil in the second configuration.

In yet another embodiment, residual pressure is maintained between the left and right legs of the formed surgical clip after the force is applied to the anvil, such that the distal ends of the left and right legs engage each other when the formed clip is established.

In one embodiment the left and right legs have a non-intersecting and non-overlapping relationship relative to each other when the formed clip is established.

In yet another embodiment, the formed surgical clip is a hemostatic clip and is made from a material selected from the group consisting of stainless steel, a polymer, titanium, a biocompatible material, and any combinations thereof. The formed surgical clip may also be a blood vessel clip.

In accordance with another aspect of the present disclosure, there is provided a method of forming a surgical clip. The method includes providing an unformed surgical clip in a first configuration having: a head section including an upper portion and a lower portion, the upper and lower portions separated from each other to define a first space therebetween, a left leg section including a proximal end and a distal end, and a right leg section including a proximal end and a distal end. The method also includes the steps of providing an anvil configured to engage the head section of the unformed surgical clip, positioning a pair of forming pins at the proximal ends of the left and right legs for securing the head section of the unformed surgical clip against the anvil, applying a force to the anvil and compressing the upper portion of the head section toward the lower portion of the head section to transform the unformed surgical clip into a formed or "T-shaped" surgical clip in a second configuration.

In accordance with an embodiment of the present disclosure, there is provided a "T-shaped" surgical clip for occluding a blood vessel. The "T-shaped" surgical clip includes a head section having an upper portion and a lower portion, a first leg section and a second leg section being substantially parallel to the first leg section. The "T-shaped" surgical clip is formed by an anvil and a pair of forming pins cooperating to (i) compress the upper portion of the head section toward the lower portion of the head section and (ii) compress the first and second legs to be in abutting relationship with respect to each other.

In one embodiment, a linear compression force is applied to the anvil to compress the upper portion of the head section toward the lower portion of the head section.

In another embodiment, residual pressure is maintained between the first and second legs after the force is applied to the anvil, such that the distal ends of the first and second legs abuttingly engage each other.

In yet another embodiment, the first and second legs have a non-intersecting and non-overlapping relationship relative to each other.

In accordance with another embodiment of the present disclosure, there is provided a surgical clip forming apparatus. The surgical clip forming apparatus includes an unformed element having a head section including an upper portion and a lower portion, a first leg section, and a second leg section, an anvil configured to engage the upper portion of the head section of the unformed element and a pair of forming pins positioned adjacent proximal ends of the first and second legs for securing the upper portion of the head section of the unformed element against the anvil. When a linear compression force is applied to the anvil, the upper portion of the head section compresses toward the lower portion of the head section in order to create a "T-shaped" surgical clip.

In one embodiment, the first and second legs extend in a substantially parallel configuration relative to each other after the linear compression force has been applied to the anvil.

In another embodiment, residual pressure is maintained between the first and second legs after the linear compression force has been applied to the anvil, such that distal ends of the first and second legs abuttingly engage each other.

In yet another embodiment, the first and second legs have a non-intersecting and non-overlapping relationship relative to each other.

BRIEF DESCRIPTION OF THE DRAWINGS

Various embodiments of the present disclosure are described hereinbelow with reference to the drawings, wherein.

DETAILED DESCRIPTION OF EMBODIMENTS

Figure 1:
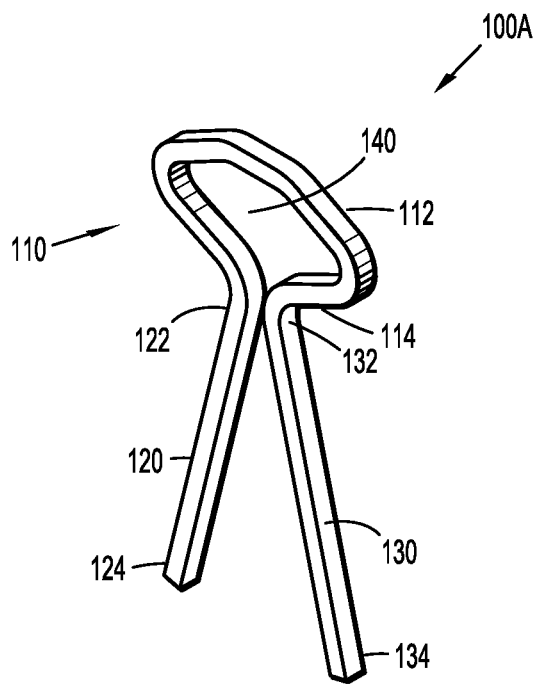
FIG. 1 is a perspective view of a surgical clip in a first configuration, in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Figure 2:
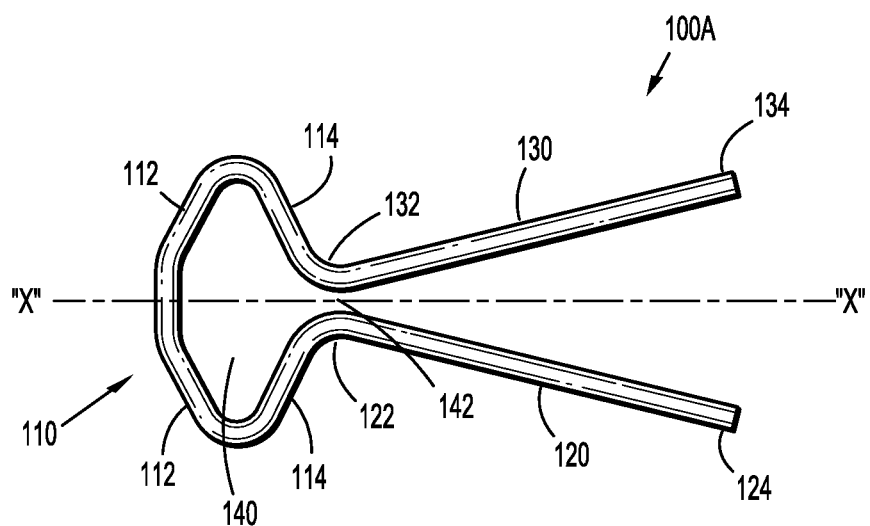
FIG. 2 is a side view of the surgical clip of FIG. 1, in accordance with an embodiment of the present disclosure.
Figure 3:
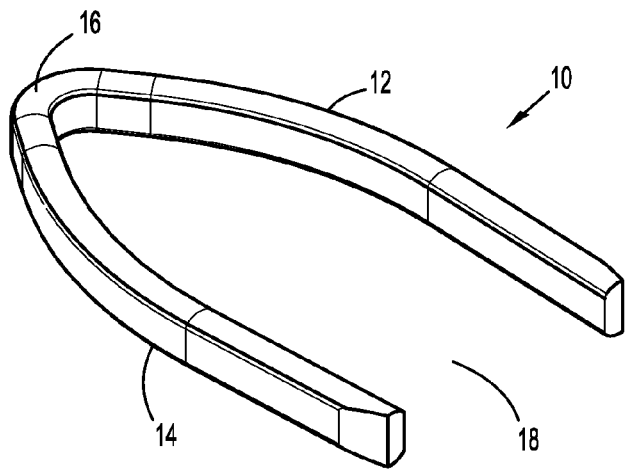
FIGS. 3-6 are views of a C-shaped surgical clip occluding a blood vessel in accordance with the conventional art.

With reference to FIGS. 1 and 2, a surgical clip 100A is presented in a first configuration. The first configuration is an uncompressed or unbiased configuration. The surgical clip 100A includes a head section 110 having an upper portion 112 and a lower portion 114, the upper and lower portions 112, 114 separated from each other to define a first space 140 therebetween. The surgical clip 100A also includes a left leg section 120 including a proximal end 122 and a distal end 124, and a right leg section 130 including a proximal end 132 and a distal end 134. FIG. 2 further illustrates a gap region 142 between the proximal ends 122, 132 of the left and right leg sections 120, 130, respectively.

Surgical clip 100A is shown in a first configuration, that is, a pre-formed configuration. In this first configuration or pre-formed configuration, no bias or no forces have been applied to any portions or sections of the surgical clip 100A. In other words, the surgical clip 100A may be pre-manufactured in this unbiased (or non-deformed) state. In this first configuration, the head section 110 of the surgical clip 100A is shown in a substantially circular or substantially oval shaped configuration. The oval or circular head portion defines a central longitudinal axis "X." The upper portion 112 of the head section 110 may include bent or curved sections, as illustrated in FIGS. 1 and 2. Stated differently, the top of the head section 110 may include an apex portion or a segmented pattern. However, one skilled in the art may contemplate a smooth surface running the length of the upper portion 112. It is contemplated, in any of the embodiments disclosed herein, that the head portion can have a polygonal shape. The leg sections of the clip extend generally along the axis X, and have their proximal ends adjacent the axis X, as opposed to being spaced therefrom as in the typical U-shaped staple or C shaped clip.

Additionally, in this first configuration, in which the clip has not been formed or deformed yet, a gap region or area 142 is present between the proximal ends 122, 132 of the left and right leg portions 120, 130, respectively. The gap region 142 is adjacent one end of the first space 140 defined within the head section 110. Moreover, the left leg section 120 and the right leg section 130 may extend away from the gap region 142 in a non-parallel manner. In other words, the left leg section 120 may extend at an angle with respect to the longitudinal axis "X" running perpendicular and substantially centrally through the upper portion 112 of the head section 110. Similarly, the right leg section 130 may extend at an angle with respect to the longitudinal axis "X" running perpendicular and substantially centrally through the upper portion 112 of the head section 110.

With reference to FIGS. 1 and 2, the surgical clip 100A in the first configuration of the subject disclosure may be of any dimension suitable for application to vessels and body tissue. In one embodiment, the length of the surgical clip 100A is about 7.95 millimeters and the width of the surgical clip 100A from an outer surface of the first leg 120 to an outer surface of the second leg 130 is about 4 to 5 millimeters, and the surgical clip 100A is intended to be used with a five millimeter cannula. One of ordinary skill in the art will recognize that other dimensions can also be used, and the dimensions of the surgical clip 100A may be modified to various other dimensions to fit various clip appliers, trocars, tissue, vessels, arteries or other surgical procedures.

Figure 5:
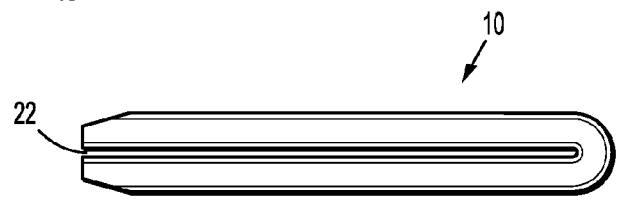
Figure 4:
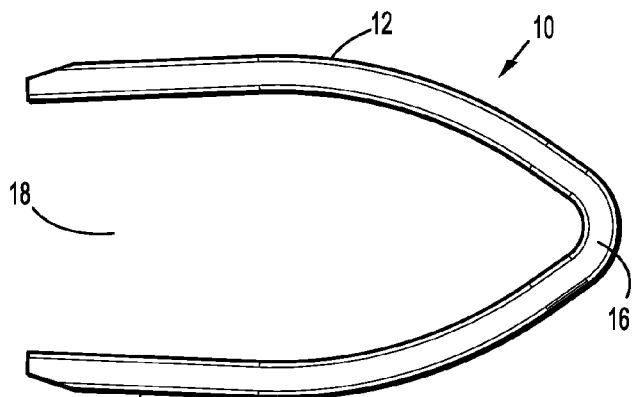
Figure 6:
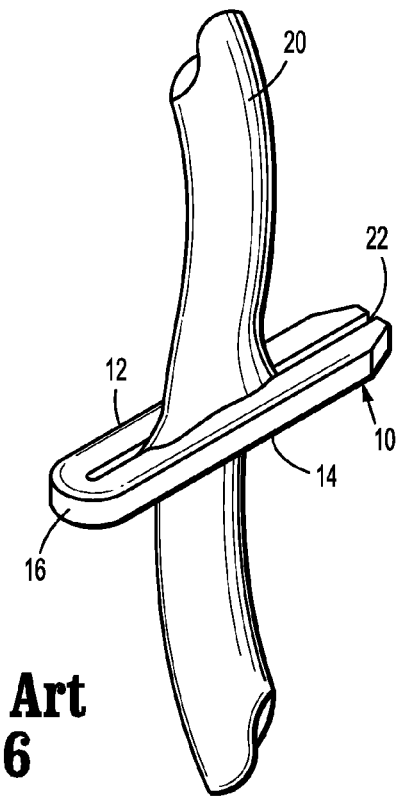

Referring to FIGS. 3-6, a conventional "C-shaped" clip 10 is presented. The C-shaped clip 10 includes a first leg 12 and a second leg 14 connected to each other via a head section 16. A gap region 18 is formed between the first and second legs 12, 14. The first and second legs 12, 14 are substantially parallel to each other. FIG. 6 depicts a blood vessel 20 occluded between the first and second legs 12, 14, when the blood vessel enters the gap region 18. Additionally, a gap region 22 is depicted in FIGS. 5 and 6, which exists when the first and second legs 12, 14 cooperate to occlude blood vessel 20.

The C-shaped clip 10 occludes the blood vessel 20 by forces applied to the sides of the first and second legs 12, 14. Side loads are applied to the first and second legs 12, 14 to bring the first leg 12 in contact with the second leg 14. As such, the C-shaped clip 10 cannot generate residual clamp pressure between the legs 12, 14 after being formed, regardless of the load or force or pressure applied to the sides of the first and second legs 12, 14. The legs 12, 14 are separate or apart from each other after the clip if formed. In other words, the gap region 22 is always present between the legs 12, 14, whether they are open or closed to occlude the blood vessel 20. The C-shaped clip does not provide for optimum retention of a blood vessel.

Figure 7:
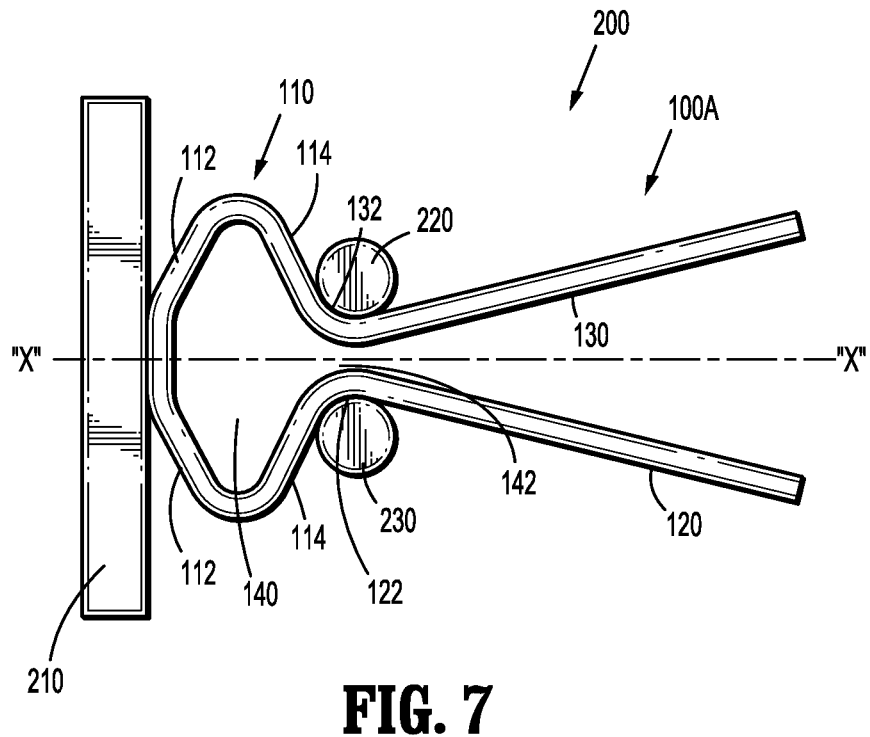
FIG. 7 is a side view of the surgical clip of FIG. 1 engaging the surgical clip forming apparatus having an anvil and a pair of pins, in accordance with an embodiment of the present disclosure.
Figure 8:
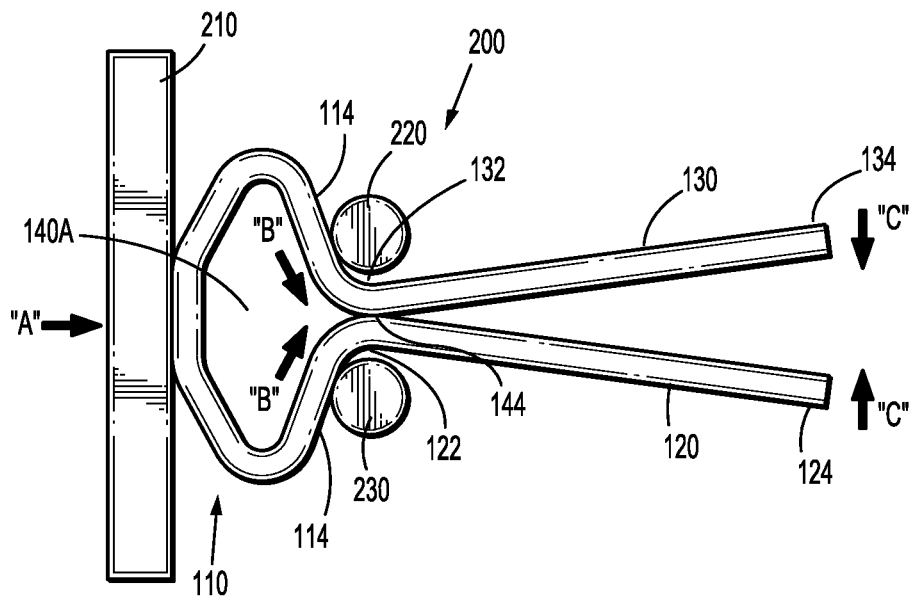
FIG. 8 is a side view of the surgical clip of FIG. 1 engaging the surgical clip forming apparatus having the anvil and the pair of pins, where a linear force is applied to the anvil to compress the surgical clip, in accordance with an embodiment of the present disclosure.

Referring to FIGS. 7 and 8, a side view of the surgical clip of FIG. 1 engaging the clip forming apparatus 200 having an anvil 210 and a pair of pins 220, 230, where a linear force "A" is applied to the anvil 210 to compress the surgical clip 100A, in accordance with an embodiment of the present disclosure is presented.

The surgical clip forming apparatus 200 includes an anvil 210 configured to engage the head section 110 of the surgical clip 100A in the first configuration. The surgical clip forming apparatus 200 further includes a pair of forming pins 220, 230. The surgical clip forming apparatus 200 facilitates the predetermined deformation of the surgical clip 100A.

The first pin 220 engages or contacts the proximal end 132 of the right leg section 130, whereas the second pin 230 engages or contacts the proximal end 122 of the left leg section 120. The pair of forming pins 220, 230 frictionally secure the head section 110 of the surgical clip 100A against the anvil 210, as shown in FIGS. 7 and 8. The pair of forming pins 220, 230 are shown to be circular. However, one skilled in the art may contemplate the pair of forming pins 220, 230 to have any shape or size, in accordance with the desired application.

When the surgical clip 100A connects or engages or cooperates with the surgical clip forming apparatus 200, the gap region 142 is still present, as shown in FIG. 7. Moreover, the left leg and right leg sections 120, 130 continue to be in a non-parallel relationship with each other (or in a non-parallel relationship with respect to the longitudinal axis "X"). However, in FIG. 8, a force "A" is applied to the anvil 210. The force "A" is a linear compression force. The linear compression force "A" is applied in a direction parallel to the longitudinal axis "X" extending through the head section 110 of the surgical clip 100A. As the linear compression force "A" is applied to the anvil 210, forces "B" are applied to the lower portion 114 of the head section 110, such that the gap region 142 is closed or blocked off. In other words, the proximal ends 122, 132 of the left and right leg sections 120, 130, respectively, move closer to each other in order to establish an engaging relationship therebetween.

As shown in FIG. 8, after forces "A" and "B" have been applied for a predetermined period of time, the proximal ends 122, 132 contact each other at a point 144 to remove the presence of the gap region 142. Additionally, the force "A" applied to the anvil 210 causes the upper head portion 112 to move closer to the lower head portion 114, such that the first space 140 is transformed into a second space 140A. The second space 140A is smaller than the first space 140 defined within the head section 110. The second space 140A defines a less circular or less oval shape as force "A" is applied to the anvil 210, which causes forces "B" to be applied to the lower head portion 114 of the head section 110.

Furthermore, FIG. 8 illustrates that, as force "A" is continuously applied to the anvil 210, the distal ends 124, 134 of the left and right leg sections 120, 130, respectively, push closer to each other, as shown by arrows "C." Stated differently, the motion or pressure applied to the anvil 210 causes the compression of the head section 110, which in turn causes the left and right leg sections 120, 130 to move toward each other since the proximal ends 122, 132 of the remain substantially in place due to the forming pins 220, 230. The forming pins 220, 230 cause the proximal ends 122, 132 to remain secure within the gap region 142. Therefore, the fixed positioning of the pins 220, 230, in tandem with the pressure applied to the anvil 210, causes the surgical clip 100A to transform or deform into a new configuration, discussed with reference to FIGS. 9-12. The clip applies residual clamp pressure even after formation, due to the configuration of the legs and the head portion, and the manner in which the clip is formed. He leg portions, particularly the proximal ends thereof, can be biased against each other. The gap or space between the legs is eliminated, allowing the legs to remain touching and applying pressure.

Figure 9:
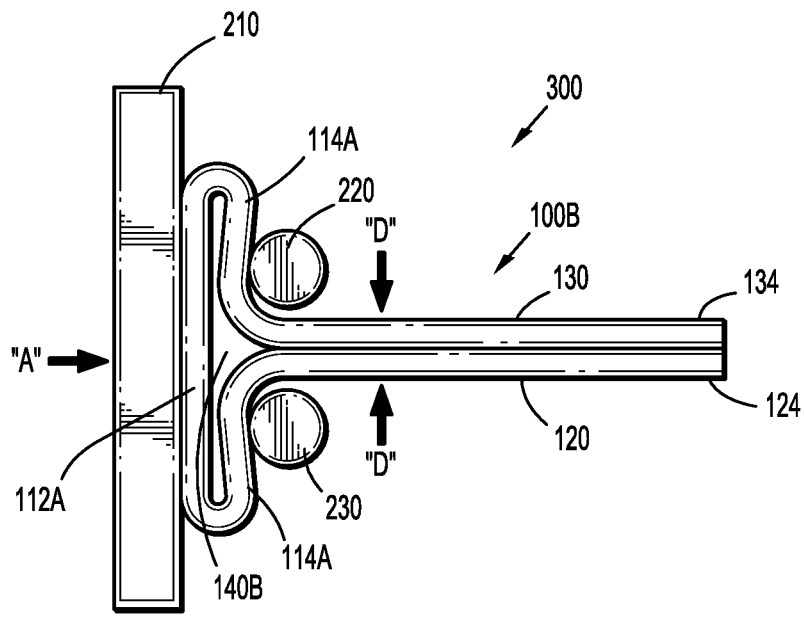
FIG. 9 is a side view illustrating the surgical clip of FIG. 1 transformed into a T-shape in a second configuration, in accordance with an embodiment of the present disclosure.
Figure 10:
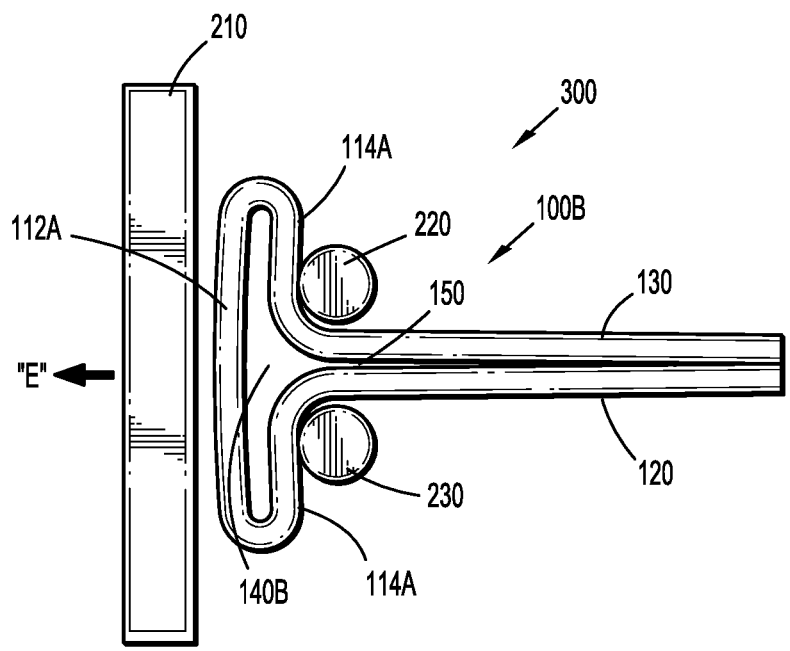
FIG. 10 is a side view of the final form of the T-shaped surgical clip in the second configuration, when a force is no longer applied to the anvil, in accordance with an embodiment of the present disclosure.

FIGS. 9 and 10 illustrate the deformation 300 of the surgical clip 100A from a first configuration into a surgical clip 100B having a second configuration. The second configuration is a deformed or biased configuration. After force "A" is applied to the anvil 210 for a predetermined period of time, the upper portion 112 of the head section 110 is compressed to be adjacent (but, not necessarily abutting) the lower portion 114 of the head section 110. Thus, the upper portion 112 has been transformed into an upper portion 112A in a second configuration and the lower portion 114 has been transformed into a lower portion 114A in a second configuration, where the upper portion 112A and the lower portion 114A are substantially parallel to each other as a result of the constant force applied to the anvil 210.

Moreover, the new space 140B defined between the upper portion 112A and the lower portion 114A has been minimized. Also, the left and right leg sections 120, 130 have been pushed together, such that the left and right leg sections 120, 130 contact each other throughout their entire length (from the proximal ends 122, 132 to the distal ends 124, 134). However, one skilled in the art may contemplate a small non-abutting space 150 between the left and right leg sections 120, 130, as shown in FIG. 10, when the anvil 210 has been disengaged and retracted away from the head portion 112A in the second configuration, in a direction "E." In other words, after the pre-loading has been overcome, a proximal region of the left and right leg sections 120, 130 may create a new gap region 150.

Additionally, as pressure or force "A" is applied to the anvil 210, forces "D" are applied to proximal ends 122, 132 of the left and right leg sections 120, 130, as shown in FIG. 9. Forces "D" are forces that are opposed to each other in order to bring the proximal regions of the left and right leg sections 120, 130 closer together. Forces "D" are caused due to the fixed positioning of the pins 220, 230 and their fixed orientational relationship with respect to the anvil 210. As noted, the left and right leg sections 120, 130 may be adjacent to each other or abut each other across their entire length or at least a portion of their length once the clip is transformed into the "T-shape."

Therefore, the "T-shaped" clip 100B is formed above the tips 124, 134 of the clip 100B, thus allowing the tips 124, 134 to remain touching with pressure between the tips 124, 134 increasing clamp retention pressure/force of the clip 100B. The forming of the T-shaped clip 100B is performed in the linear compression direction. The linear compression comes from the handle (not shown) of the anvil 210 to form the "T-shape" of the clip 100B. As such, residual pressure is maintained between the left and right leg sections 120, 130 of the clip 100B. Additionally, it is noted that the left leg section 120 is non-overlapping and non-intersecting with respect to the right leg portion 130. Stated differently, no portions of the length of the left leg section 120 overlap and/or intersect with the right leg section 130.

Figure 11:
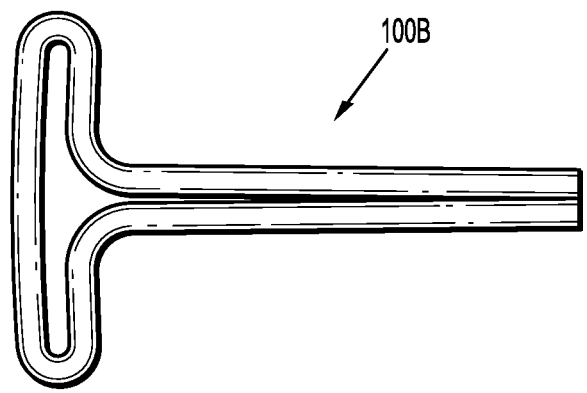
FIGS. 11 and 12 are side and perspective views of the surgical clip in the second configuration, where the surgical clip has been transformed into a T-shaped configuration, in accordance with an embodiment of the present disclosure.
Figure 12:
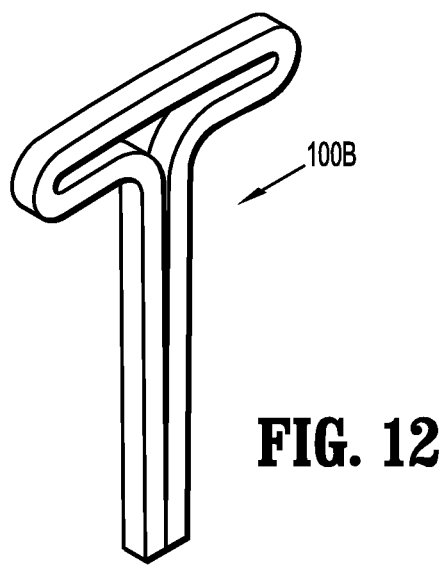
Figure 13:
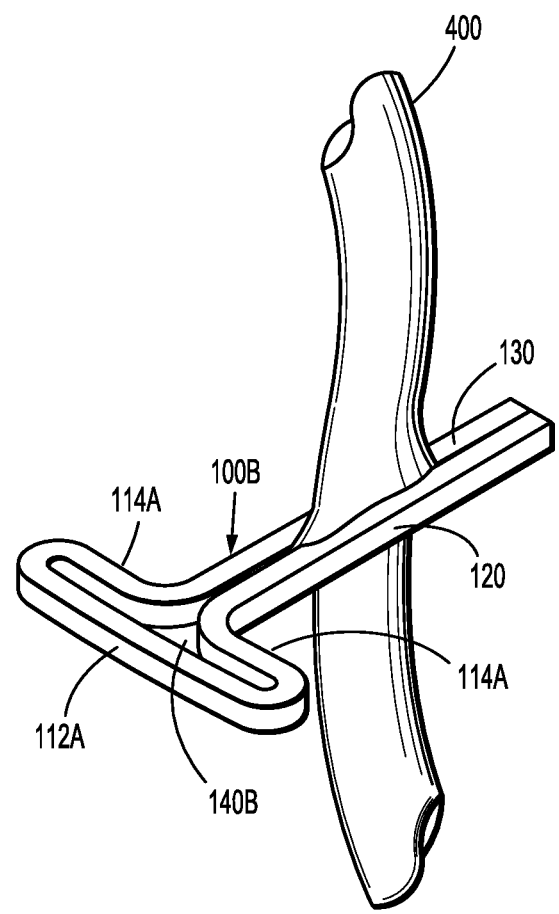
FIG. 13 is a perspective view of the T-shaped clip occluding a blood vessel, in accordance with another embodiment of the present disclosure.

With reference to FIGS. 11-13, side and perspective views of the surgical clip 100B in the second configuration, where the surgical clip 100B has been transformed into a T-shaped configuration for occluding a blood vessel 400, in accordance with an embodiment of the present disclosure is presented.

The surgical clip 100B of FIGS. 11-13 may be used with various different clip geometries and the present disclosure is not limited to any specific clip geometry. Each of the legs 120 and 130 of surgical clip 100B may define a respective tissue gripping surface on a lateral side of the hemostatic clip 100B. It is envisioned that the desired tissue, such as an artery, vessel or vein is clamped between the tissue gripping surfaces between the legs 120, 130 during application of the surgical clip 100B for occlusion, or notably the obstruction or a closure of a passageway or vessel. As used herein, the term "gripping pattern" means any arrangement, structure or pattern that promotes exudation of tissue. The gripping pattern assists with the compressed or deformed clip 100B being retained on the vessel for occlusion purposes. As used herein, the term "tissue exudation" means the process upon which the tissue gradually moves, oozes or traverses into a recess, cavity, lateral surface, apex, distal end, chamfer, textured surface or structure of the clip to remain frictionally engaged thereon such that the clip remains on the desired tissue without damaging the vessel or tissue until physically removed or with degradable clips, until the clip disintegrates.

The surgical clips 100A, 100B of the present disclosure may be fabricated from any biocompatible material including stainless steel, titanium, and tantalum, as well as plastic materials including biocompatible polymers, or a combination of materials thereof.

It is contemplated that, in any of the embodiments disclosed herein, the legs are parallel to one another prior to the formation of the clip. Furthermore, fasteners such as clips or staples can have the T-shaped or bow-shaped configuration disclosed herein. It is also contemplated that, in any of the embodiments disclosed herein, other means of forming the clip or staple, or deforming the clip or staple into a closed configuration, can be used. An instrument that is manually or electromechanically powered, or otherwise powered, can be used to form the fasteners.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

What is claimed is:

1. A surgical clip forming apparatus, comprising:
   an unformed surgical clip including:
      an oval-shaped head section including an upper portion and a lower portion, the upper and lower portions separated from each other to define a first space therebetween in a first configuration;
      a left leg section including a proximal end and a distal end; and
      a right leg section including a proximal end and a distal end;

an anvil configured to engage the oval-shaped head section of the unformed surgical clip; and a pair of forming pins positioned adjacent the proximal ends of the left and right legs for securing the oval-shaped head section of the unformed surgical clip against the anvil;

wherein, when a force is applied to a planar surface of the upper portion of the oval-shaped head section, the upper portion of the oval-shaped head section compresses toward the lower portion of the oval-shaped head section in order to define a formed clip.

2. The apparatus according to claim 1, wherein the force applied to the anvil is a linear compression force.

3. The apparatus according to claim 1, wherein the lower portion of the oval-shaped head section includes a gap region between the pair of forming pins in the first configuration.

4. The apparatus according to claim 3, wherein the unformed surgical clip transforms into a "T-shaped" clip, which is the formed clip in a second configuration, after the force has been applied to the anvil, such that the upper and lower portions are separated from each other to define a second space therebetween, the second space being less than the first space.

5. The apparatus according to claim 4, wherein the gap region disappears after the force has been applied to the anvil to transform the unformed clip to the second configuration.

6. The apparatus according to claim 4, wherein the left and right legs extend in a substantially parallel configuration relative to each other, from the proximal ends to the distal ends thereof, after the force has been applied to the anvil to transform the unformed clip to the second configuration.

7. The apparatus according to claim 1, wherein residual pressure is maintained between the left and right legs of the formed surgical clip after the force is applied to the anvil, such that the distal ends of the left and right legs engage each other when the formed clip is defined.

8. The apparatus according to claim 1, wherein the left and right legs have a non-intersecting and non-overlapping relationship relative to each other when the formed clip is defined.

9. The apparatus according to claim 1, wherein the formed surgical clip is a hemostatic clip and is made from a material selected from the group consisting of stainless steel, a polymer, titanium, a biocompatible material, and any combinations thereof.

10. The apparatus according to claim 1, wherein the formed surgical clip is a blood vessel clip.

11. A method of forming a surgical clip, the method comprising:

providing an unformed surgical clip in a first configuration having:

an oval-shaped head section including an upper portion and a lower portion, the upper and lower portions separated from each other to define a first space therebetween;

a left leg section including a proximal end and a distal end; and a right leg section including a proximal end and a distal end;

providing an anvil configured to engage the oval-shaped head section of the unformed surgical clip;

positioning a pair of forming pins at the proximal ends of the left and right leg sections for securing the oval-shaped head section of the unformed surgical clip against the anvil;

applying a force to a planar surface of the upper portion of the oval-shaped head section; and compressing the upper portion of the oval-shaped head section toward the lower portion of the oval-shaped head section to transform the unformed surgical clip to a formed surgical clip in a second configuration.

12. The method according to claim 11, wherein the force applied to the anvil is a linear compression force.

13. The method according to claim 11, wherein the lower portion of the oval-shaped head section includes a gap region between the pair of forming pins in the first configuration.

14. The method according to claim 13, wherein the unformed surgical clip transforms into a "T-shaped" clip, which is the formed clip in the second configuration, such that the upper and lower portions are separated from each other to define a second space therebetween, the second space being less than the first space.

15. The method according to claim 14, wherein the gap region disappears after the force has been applied to the anvil to transform the unformed clip to the second configuration.

16. The method according to claim 14, wherein the left and right leg sections extend in a substantially parallel configuration relative to each other after the force has been applied to the anvil to transform the unformed clip to the second configuration.

17. The method according to claim 11, wherein residual pressure is maintained between the left and right leg sections of the formed surgical clip after the force is applied to the anvil, such that the distal ends of the left and right leg sections engage each other when the formed clip is defined.

18. The method according to claim 11, wherein the left and right leg sections have a non-intersecting and non-overlapping relationship relative to each other when the formed clip is defined.

19. The method according to claim 11, wherein the formed surgical clip is a hemostatic clip and is made from a material selected from the group consisting of stainless steel, a polymer, titanium, a biocompatible material, and any combinations thereof.

20. The method according to claim 11, wherein the formed surgical clip is a blood vessel clip.

21. A surgical clip forming apparatus, comprising:

an unformed element having an oval-shaped head section including an upper portion and a lower portion, a first leg section, and a second leg section;

an anvil configured to engage the upper portion of the oval-shaped head section of the unformed element; and a pair of forming pins positioned adjacent proximal ends of the first and second leg sections for securing the upper portion of the oval-shaped head section of the unformed element against the anvil;

wherein, movement of the anvil applies a linear compression force to a planar surface of the upper portion of the oval-shaped head section, the upper portion of the oval-shaped head section compresses toward the lower portion of the oval-shaped head section in order to define a "T-shaped" surgical clip.

22. The surgical clip forming apparatus according to claim 21, wherein the first and second leg sections extend in a substantially parallel configuration relative to each other, along their entire length, after the linear compression force has been applied to the anvil.

23. The surgical clip forming apparatus according to claim 21, wherein residual pressure is maintained between the first and second leg sections after the linear compression force has been applied to the anvil, such that distal ends of the first and second leg sections abuttingly engage each other.

24. The surgical clip forming apparatus according to claim 21, wherein the first and second leg sections have a non-intersecting and non-overlapping relationship relative to each other.

\* \* \* \* \*